(12) United States Patent
Yokohata et al.

(10) Patent No.: US 8,794,029 B2
(45) Date of Patent: Aug. 5, 2014

(54) PROCESS AND APPARATUS FOR SEPARATION OF HYDROCARBONS FROM LIQUEFIED NATURAL GAS

(75) Inventors: Hiroshi Yokohata, Narashino (JP); Shoichi Yamaguchi, Narashino (JP); Akihiko Tamakoshi, Narashino (JP)

(73) Assignee: Toyo Engineering Corporation, Tokyo (JP)

( * ) Notice: Subject to any disclaimer, the term of this patent is extended or adjusted under 35 U.S.C. 154(b) by 704 days.

(21) Appl. No.: 11/452,221

(22) Filed: Jun. 14, 2006

(65) Prior Publication Data

US 2006/0277943 A1 Dec. 14, 2006

(30) Foreign Application Priority Data

Jun. 14, 2005 (JP) ................... 2005-173461

(51) Int. Cl.
*F25J 3/00* (2006.01)
*F25J 3/02* (2006.01)

(52) U.S. Cl.
CPC ............ *F25J 3/0214* (2013.01); *F25J 2210/62* (2013.01)
USPC .................................. 62/620; 62/630; 62/50.2

(58) Field of Classification Search
CPC ............................. F25J 3/0214; F25J 2210/62
USPC ............................................ 62/620, 623, 630
See application file for complete search history.

(56) References Cited

U.S. PATENT DOCUMENTS

| | | | | |
|---|---|---|---|---|
| 2,127,004 A | * | 8/1938 | Nelson | 62/623 |
| 2,534,274 A | * | 12/1950 | Kniel | 62/628 |
| 2,916,888 A | * | 12/1959 | Cobb, Jr. | 62/623 |
| 2,953,905 A | * | 9/1960 | Chrones et al. | 62/630 |
| 3,367,122 A | * | 2/1968 | Tutton | 62/630 |
| 3,393,527 A | * | 7/1968 | Swenson et al. | 62/621 |
| 3,405,530 A | * | 10/1968 | Denahan et al. | 62/630 |
| 3,456,032 A | | 7/1969 | Kniel | |
| 3,456,037 A | | 7/1969 | Hoeschele | |
| 3,524,897 A | | 8/1970 | Kniel | |

(Continued)

FOREIGN PATENT DOCUMENTS

GB 1438213 6/1976

OTHER PUBLICATIONS

Nielsen et al., "L N G Flexibility," Hydrocarbon Engineering, pp. 26-31 (Oct. 2003).

(Continued)

*Primary Examiner* — John F Pettitt
(74) *Attorney, Agent, or Firm* — Fitch, Even, Tabin & Flannery LLP

(57) ABSTRACT

A process for separating hydrocarbons from an LNG, including the steps of: distilling a feed LNG in a first distillation column to separate it into a fraction enriched with methane and a fraction enriched with components heavier than methane; distilling the fraction enriched with components heavier than methane in a second distillation column to separate it into a fraction enriched with ethane and a fraction enriched with components heavier than ethane; recovering the cryogenic heat of the feed LNG to be fed into the first distillation column or of the liquid inside the first distillation column by using a heat transfer medium; and cooling the overhead gas of the second distillation column by using the heat transfer medium which has recovered the cryogenic heat to condense at least part of the overhead gas of the second distillation column. An apparatus for carrying out this process.

12 Claims, 6 Drawing Sheets

(56) References Cited

U.S. PATENT DOCUMENTS

| | | | |
|---|---|---|---|
| 3,548,024 A | | 12/1970 | Kniel |
| 3,548,029 A | | 12/1970 | Stahly et al. |
| 3,849,096 A | * | 11/1974 | Kniel ............... 62/631 |
| 4,411,677 A | * | 10/1983 | Pervier et al. ........... 62/622 |
| 4,778,498 A | * | 10/1988 | Hanson et al. ........... 62/623 |
| 5,457,951 A | * | 10/1995 | Johnson et al. ........... 60/780 |
| 6,158,240 A | * | 12/2000 | Low et al. ............... 62/611 |
| 2003/0158458 A1 | * | 8/2003 | Prim ..................... 585/800 |
| 2005/0155381 A1 | * | 7/2005 | Yang et al. ............. 62/620 |
| 2008/0190106 A1 | * | 8/2008 | Mak .................... 60/531 |
| 2008/0307789 A1 | * | 12/2008 | Mak .................... 60/651 |

OTHER PUBLICATIONS

Yang et al., "Cost-effective design reduces $C_2$ and $C_3$ at LNG receiving terminals," Oil & Gas Journal pp. 50-53 (May 2003).

* cited by examiner

PROCESS AND APPARATUS FOR SEPARATION OF HYDROCARBONS FROM LIQUEFIED NATURAL GAS

This Application is a U.S. Nonprovisional Utility Patent Application which claims foreign priority from Japanese Application No. 2005-173461, filed Jun. 14, 2005, the complete disclosure of which is incorporated herein by reference.

BACKGROUND

1. Field of the Invention

The present invention relates to a process and apparatus for separation of hydrocarbons, used for separating and recovering hydrocarbons such as ethane, propane, butane and the like from a liquefied natural gas.

2. Background of the Invention

It is being conducted generally to liquefy a natural gas at about −162° C. at around atmospheric pressure, send the liquefied natural gas to a marketplace by marine transportation, vaporize the liquefied natural gas, and then feed it into a natural gas pipeline as a town gas or a fuel for thermal power generation. Incidentally, a natural gas liquefied at around atmospheric pressure is called liquefied natural gas (LNG). The liquefied natural gas received at the marketplace contains, in some cases, a large amount of hydrocarbons composed of ethane, propane, butane and a small amount of heavier components. Such a liquefied natural gas has a high calorific value and therefore may not meet the natural gas specification required by the marketplace. Or, the hydrocarbons such as ethane, propane, butane and the like, contained in liquefied natural gas can be used as a raw material for petrochemical plants and therefore have, in some cases, a higher commercial value than when used as a town gas or as a fuel for thermal power generation. Hence, it has been desired to separate and recover hydrocarbons such as ethane, propane, butane and the like from a liquefied natural gas received by the marketplace before the natural gas is fed into a natural gas pipeline.

In order to separate and recover, from a liquefied natural gas, a fraction containing components heavier than methane, it is necessary to vaporize a major portion of the liquefied natural gas. Therefore, the reboiler of a demethanizer needs a large amount of heat. The feeding of heat to the reboiler of the distillation column is generally conducted by a method of direct heating using a heat medium such as steam or by a method wherein a thermal medium such as hot oil is circulated. In any method, however, generation of steam or heating of oil is necessary, consuming a large amount of a fuel.

In order to reduce the heat amount required by the reboiler of the demethanizer, it has been known to heat the liquefied natural gas fed to the demethanizer, by utilizing the sensible heat of air. By replacing part of the heating by the reboiler with heating by air, it is possible to reduce the amount of the fuel consumed for the reboiler of the demethanizer. However, the air-heated heater requires a very large heat transfer area for heat exchange; further, a structure for supporting the heater and a sufficient space for the structure are required; therefore, an improvement in investment cost is desired.

Meanwhile, in a process for separating and recovering, from a liquefied natural gas, a fraction containing components heavier than methane, the heavy fraction obtained from the bottom of the demethanizer need be separated into products such as ethane, propane and butane, for utilization of these individual products. Accordingly, there are installed, in addition to the demethanizer, a deethanizer, a depropanizer, etc.

In Non-patent Literature 1 or Non-patent Literature 2, it is described that, in such a process, a liquefied natural gas is introduced into the condenser (overhead condenser) of a deethanizer to conduct heat exchange between the liquefied natural gas and the overhead gas of the deethanizer, whereby the condensation of the overhead gas and the heating of the liquefied natural gas are simultaneously conducted.

[Non-patent Literature 1] J. Mark et al., "LNG Flexibility", Hydrocarbon Engineering, October 2003

[Non-patent Literature 2] C. C. Yang et al., "Cost-effective design reduces C2 and C3 at LNG receiving terminals", Oil & Gas Journal, May 26, 2003

SUMMARY OF THE INVENTION

When a liquefied natural gas is introduced into the overhead condenser of a deethanizer and is utilized as a cooling medium, the liquefied natural gas is heated by the overhead gas of the deethanizer. As a result, the amount of fuel consumption of the reboiler of the demethanizer can be reduced without using an air-heated heater, and energy saving and cost reduction can be achieved.

However, the easiness and reliability of operation are impaired because the overhead gas of the deethanizer or depropanizer is condensed by the liquefied natural gas which is a feed fluid to the demethanizer.

For example, when fluctuation occurs in the feed amount of liquefied natural gas, the fluctuation immediately affects the deethanizer, disturbing the operation of the deethanizer.

Also, when there occurs a breakage of a heat exchanger (an overhead condenser) which exchange heat between liquefied natural gas and the overhead gas of the deethanizer, there is a possibility that a liquefied natural gas as cold as −160° C. flows into the deethanizer. Since the deethanizer is not designed generally for such a low temperature, the incoming of such a liquefied natural gas gives thermal shock to the deethanizer, damaging the deethanizer. As a countermeasure therefor, it is considered to manufacture a deethanizer using a material (e.g. stainless steel) capable of withstanding a temperature of about −160° C.; however, this impairs the economy.

Further, the heat transfer area of the overhead condenser becomes excessive in turndown operation (partial load operation), which may invites super-cooling of the overhead gas of the deethanizer. When the super-cooled reflux is fed into the deethanizer, the deethanizer undergoes thermal shock and is damaged.

An object of the present invention is to provide a process and apparatus capable of separating hydrocarbons such as ethane from a liquefied natural gas at a low energy at a low cost without impairing the easiness and reliability of operation.

The present invention provides a process for separating hydrocarbons from a liquefied natural gas, which includes:

(a) a step of distilling a feed liquefied natural gas in a first distillation column to separate the feed liquefied natural gas into a fraction enriched with methane and a fraction enriched with components heavier than methane;

(b) a step of distilling the fraction enriched with components heavier than methane in a second distillation column to separate the fraction enriched with components heavier than methane into a fraction enriched with ethane and a fraction enriched with components heavier than ethane;

(c) a step of recovering the cryogenic heat of the feed liquefied natural gas to be fed into the first distillation column or of the liquid inside the first distillation column by using a heat transfer medium; and (d) a step of cooling the overhead gas of the second distillation column by using the heat transfer medium which has recovered the cryogenic heat to condense at least part of the overhead gas of the second distillation column.

It is preferred that, in the step (c), the liquid inside the first distillation column is withdrawn at a position of the first distillation column lower than the position where the feed liquefied natural gas is fed, the cryogenic heat of the withdrawn liquid is recovered by using the heat transfer medium, and then the withdrawn liquid is returned into the first distillation column.

The above process may further include:

(e) a step of distilling the fraction enriched with components heavier than ethane in a third distillation column to separate the fraction enriched with components heavier than ethane into a fraction enriched with propane and a fraction enriched with components heavier than propane; and (f) a step of cooling the overhead gas of the third distillation column by using the heat transfer medium which has recovered the cryogenic heat to condense at least part of the overhead gas of the third distillation column.

The present invention provides an apparatus for separating hydrocarbons from a liquefied natural gas, which includes:

a first distillation column for distilling a feed liquefied natural gas to separate the feed liquefied natural gas into a fraction enriched with methane and a fraction enriched with components heavier than methane;

a second distillation column for distilling the fraction enriched with components heavier than methane to separate the fraction enriched with components heavier than methane into a fraction enriched with ethane and a fraction enriched with components heavier than ethane;

a heat exchanger for recovering the cryogenic heat of the feed liquefied natural gas to be fed into the first distillation column or of the liquid inside the first distillation column by using a heat transfer medium; and a condenser for cooling the overhead gas of the second distillation column by using the heat transfer medium which has recovered the cryogenic heat to condense at least part of the overhead gas of the second distillation column.

It is preferred that, in the above apparatus, the first distillation column is provided with a line for withdrawing the liquid inside the first distillation column at a position of the first distillation column lower than the position where the feed liquefied natural gas is fed and returning the withdrawn liquid into the first distillation column, and the heat exchanger is provided in the line.

The above apparatus may further include:

a third distillation column for distilling the fraction enriched with components heavier than ethane to separate the fraction enriched with components heavier than ethane into a fraction enriched with propane and a fraction enriched with components heavier than propane; and a condenser for cooling the overhead gas of the third distillation column by using the heat transfer medium which has recovered the cryogenic heat to condense at least part of the overhead gas of the third distillation column.

According to the present invention, there is provided a process and apparatus capable of separating hydrocarbons such as ethane from a liquefied natural gas at a low energy at a low cost without impairing the easiness and reliability of operation.

1: demethanizer; 2: demethanizer overhead gas condenser; 3: demethanizer reflux drum; 4: demethanizer reboiler; 5: intermediate-stage heat exchanger of demethanizer; 6: pressurization pump for feed liquefied natural gas; 7: withdrawal pump for product liquefied natural gas; 8: residue gas compressor; 9: pressurized residue gas heat exchanger; 11: deethanizer; 12: deethanizer overhead gas condenser; 13: deethanizer reflux drum; 14: deethanizer reboiler; 21: depropanizer; 22: depropanizer overhead gas condenser; 23: depropanizer reflux drum; 24: depropanizer reboiler; 31: heat transfer medium surge drum; 32: heat transfer medium circulation pump; 61: air-heated heater; 62: demethanizer feed preheater; 63: antifreezing solution circulation pump; 101: feed liquefied natural gas; 103: demethanizer feed; 104: demethanizer overhead gas; 105: fluid obtained by cooling demethanizer overhead gas in condenser; 106: demethanizer reflux; 107: residue gas; 108: pressurized residue gas; 109: liquefied pressurized residue gas; 151: line for withdrawal of demethanizer-inside liquid; 152: line for returning of line 151; 191: product liquefied natural gas; 201: deethanizer feed (demethanizer bottom liquid); 202: deethanizer overhead gas; 203: fluid obtained by cooling deethanizer overhead gas in condenser; 204: deethanizer reflux; 205: product ethane; 301: depropanizer feed (deethanizer bottom liquid); 302: depropanizer overhead gas; 304: depropanizer reflux; 305: product propane; 401: product butane; 501: heat transfer medium heated by deethanizer condenser or depropanizer condenser; 502: heat transfer medium cooled by intermediate-stage heat exchanger; 505: heat transfer medium fed to deethanizer condenser; 506: heat transfer medium heated by deethanizer condenser; 515: heat transfer medium fed to depropanizer condenser; 516: heat transfer medium heated by depropanizer condenser; 601: antifreezing solution heated by air-heated heater; 602: antifreezing solution cooled by demethanizer feed preheater

DETAILED DESCRIPTION OF THE INVENTION

Embodiments of the present invention are explained below with reference to the attached drawings. However, the present invention is not limited thereby.

Figure 1:
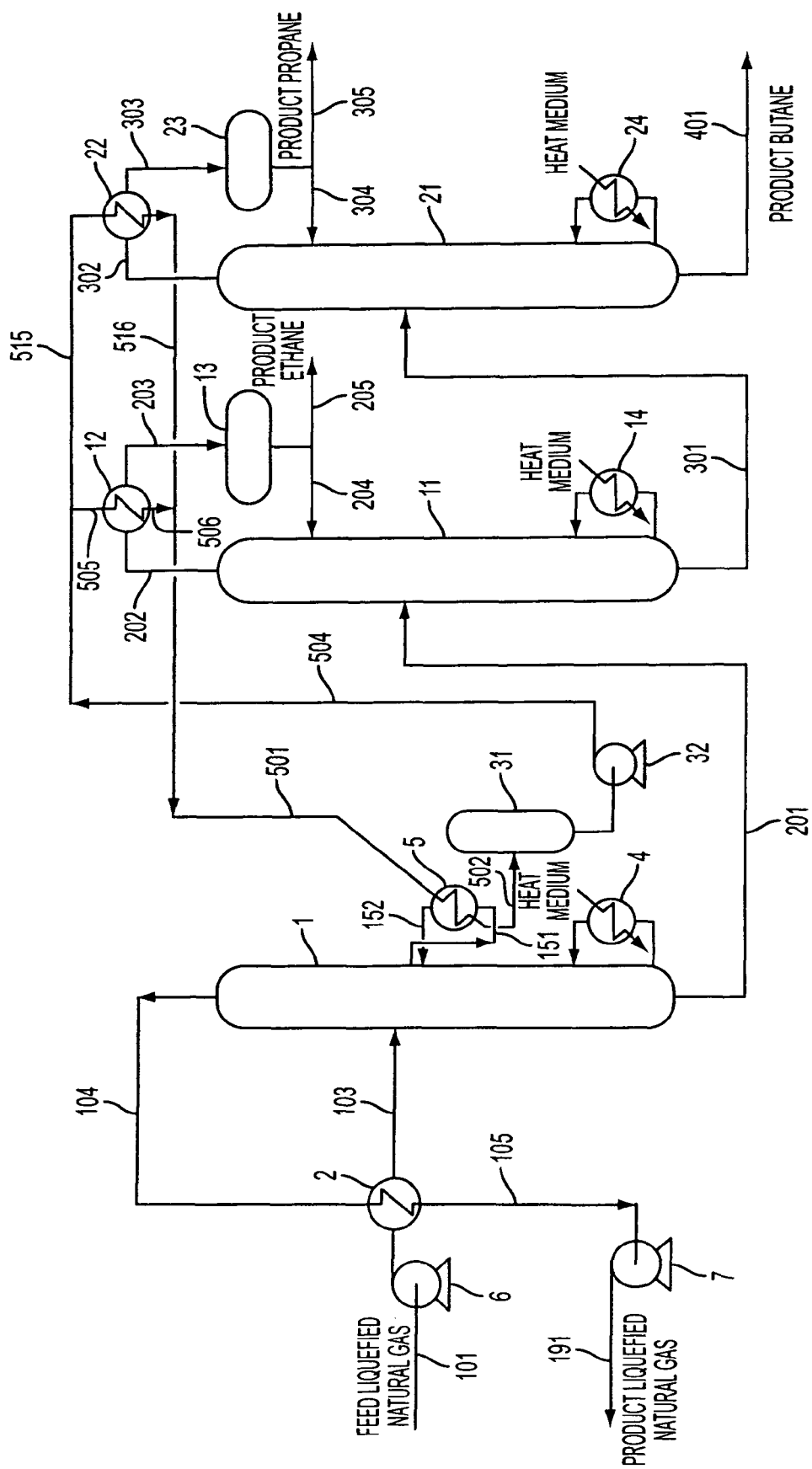
FIG. 1 is a flow diagram for explaining an embodiment of the apparatus of the present invention for separating hydrocarbons from a liquefied natural gas.

In FIG. 1 is shown an outline of an embodiment of the apparatus of the present invention for separating hydrocarbons from a liquefied natural gas. Here is explained a process for recovering ethane, propane and butane from a liquefied natural gas to be treated (a feed liquefied natural gas).

In this process, first, a liquefied natural gas is separated into methane and components heavier than methane by a first distillation column, i.e. demethanizer 1; then, the components heavier than methane are separated into ethane and components heavier than ethane by a second distillation column, i.e. deethanizer 11; further, the components heavier than ethane are separated into propane and components heavier than propane by a third distillation column, i.e. depropanizer 21.

For each of the demethanizer, the deethanizer and the depropanizer, a known distillation column structure can be used as appropriate. For example, trays or packing are installed inside the column to enable separation of more volatile components from less volatile components. Their materials can be determined as appropriate depending upon the operation temperature of the column. For example, considering that the demethanizer treats a liquefied natural gas of about −100° C., a material capable of withstanding low temperatures, such as stainless steel, is preferably used for the demethanizer. In the deethanizer, a material such as killed steel is preferably used when the temperature of the top of the column falls to, for example, about −20° C. In the depropanizer where no cryogenic liquid is treated, carbon steel, which is economically efficient, is preferably used.

Feed liquefied natural gas 101 is pressurized by pressurization pump 6 for feed liquefied natural gas, is heated by undergoing heat exchange with overhead gas 104 of the demethanizer in demethanizer overhead gas condenser 2, and is fed into demethanizer 1 as demethanizer feed 103.

From the top of the demethanizer is separated overhead gas 104 from which components such as ethane and propane have been removed and which is composed mainly of methane. The overhead gas 104 is then sent to demethanizer overhead gas condenser 2, and is wholly liquefied by undergoing heat exchange with the feed liquefied natural gas. This liquid passes through line 105, is pressurized by withdrawal pump 7, and is withdrawn as product liquefied natural gas 191.

In some cases, demethanizer overhead gas 104 as-is may be withdrawn as a product. That is, condenser 2 and withdrawal pump 7 need not be used. If overhead gas 104 is wholly liquefied, the power required for pressurizing the product can be made relatively small in a case such that the product 191 is fed into pipeline. Further, by heating the feed liquefied natural gas by condenser 2, there is an advantage that the duty of reboiler 4 of the demethanizer can be reduced.

Intermediate-stage heat exchanger 5 fitted to demethanizer 1 is a heat exchanger for recovering cryogenic heat. The liquid inside the demethanizer is withdrawn (line 151); in this heat exchanger, the withdrawn liquid is heated by heat transfer medium 501; the heated liquid is returned into the demethanizer (line 152). Thereby, the cryogenic heat of the liquid inside the demethanizer is recovered by the heat transfer medium. The fluid in line 152 may retain a liquid state but may be partially or wholly gaseous. The position at which the inside liquid is withdrawn from the demethanizer is preferably determined so that the duty of reboiler 4 of the demethanizer becomes as small as possible. In this case, it is also considered that, in deethanizer overhead gas condenser 12 and depropanizer overhead gas condenser 22, desired amounts of deethanizer overhead gas 202 and depropanizer overhead gas 302 are cooled and condensed by the heat transfer medium, respectively.

Preferably, the demethanizer-inside liquid is withdrawn at a position of the demethanizer lower than the demethanizer position at which the feed natural gas is fed (the demethanizer position to which line 103 is connected), the cryogenic heat of the withdrawn liquid is recovered by the heat transfer medium, and the liquid whose cryogenic heat has been recovered is returned to the demethanizer. The reason is that the liquid withdrawn into the intermediate-stage heat exchanger does not satisfy the intended concentration of product and, by returning the fluid which has been heated and gasified at least partially into the demethanizer inside, the intermediate-stage heat exchanger can function as a reboiler. Thereby, the duty of a main reboiler installed at the bottom of the demethanizer can be reduced.

For the part for withdrawing the inside-liquid toward the intermediate-stage heat exchanger, there may be used, for example, a tray having a known chimney structure. When using the tray of this structure, a piping for returning the fluid after heat exchange to the demethanizer is fitted preferably right below the tray of chimney structure. The reason is that, when the fluid returned from the intermediate-stage heat exchanger is a two-phase flow, the gas separated in the demethanizer is passed through the chimney portion of the tray and thereby good aligning of the gas flow can be obtained.

Preferably, the temperature of the heat transfer medium at the outlet (line 502) of the heat exchanger for recovering cryogenic heat is monitored and, in order for the temperature to be at a desired level, the withdrawal amount of the demethanizer-inside liquid (the flow rate of line 151) is adjusted. Thereby, the temperature of the heat transfer medium fed to the overhead gas condensers of the deethanizer and the like can be controlled and the operational stabilities of the deethanizer and the like can be improved. For this purpose, it is possible to install a temperature sensing means such as thermocouple in line 502, a flow control valve in line 151, and a control means such as a temperature controller or computer for manipulating the flow control valve based on the sensed temperature and a set temperature.

Also, the flow rate of the heat transfer medium fed to the overhead gas condensers of the deethanizer, etc. can be visualized by the flow control and, thereby, the deethanizer, etc. can be controlled easily.

For example, it is possible to monitor the condensate temperatures of outlet lines 203 and 303 of the overhead gas condensers of the deethanizer and the depropanizer and, in order for the temperatures to be kept at desired levels, bypass part of the heat transfer medium to be fed to each overhead gas condenser and thereby adjust the flow rate of the heat transfer medium actually fed to each overhead gas condenser. Specifically, it is possible, for example, to install a bypass line (not shown in FIG. 1) connecting line 505 and line 506 without passing through condenser 12 and adjust the flow rate of the heat transfer medium passing through condenser 12. For intermediate-stage heat exchanger 5, there can be used a known heat exchanger such as multi-tubular heat exchanger as appropriate. The material therefor can be appropriately selected from known materials for heat exchanger usable at low temperatures, such as stainless steel as appropriate.

Here, the cryogenic heat of the inside liquid of the demethanizer is recovered. Alternatively, the cryogenic heat of the feed liquefied natural gas fed to the demethanizer may be recovered. The cryogenic heat of the liquefied natural gas can be recovered by a heat transfer medium, for example, by installing a heat exchanger in line 103 and conducting heat exchange between the liquefied natural gas and the heat transfer medium.

The heat transfer medium is a fluid, and is preferably a liquid under the conditions it is used, from the standpoints of the required volume and efficiency in heat exchange. For example, considering that the heat transfer medium is heat-exchanged with a natural gas of about −100° C. and further with the overhead gas of depropanizer, the heat transfer medium may have a freezing point of −90° C. or lower and a boiling point of 50° C. or higher. The heat transfer medium may be, for example, an alcohol and, when the availability is considered, methanol is preferred.

Heat transfer medium 502 which has acquired a cryogenic heat is sent to surge drum 31. Surge drum 31 is preferably installed in order to keep an appropriate static liquid head at the suction inlet of pump 32 and prevent the generation of cavity bubbles. The surge drum may be, for example, a cylindrical pressure vessel having a head at each end. The volume thereof can be appropriately selected in consideration of the stable operation of the pump. The material for the surge drum is preferably selected from those materials capable of withstanding low temperatures, such as stainless steel, in considering a possibility that the demethanizer-inside liquid of, for example, −100° C. may flow into the surge drum when intermediate-stage heat exchanger 5 has broken.

Heat transfer medium 502 of, for example, −45° C., which has acquired a cryogenic heat, is pressurized by pump 32 for circulation of heat transfer medium, is sent via line 504 to deethanizer overhead gas condenser 12 and depropanizer overhead gas condenser 22, and is used as a cooling medium for the two condensers. For each of these condensers, a known heat exchanger such as multi-tubular heat exchanger can be used. The material therefor can be selected from known materials for heat exchanger, such as stainless steel, as appropriate.

When a shell-and-tube heat exchanger is used for the heat exchanger using the heat transfer medium, it is preferred to pass the heat transfer medium through the tube side. It is because, in this case, the heat exchanger can be easily designed so as to have a high pressure resistance capable of withstanding the pressure of liquefied natural gas flown into the heat exchanger when the heat exchanger has broken.

At the bottom portions of the demethanizer, the deethanizer and the depropanizer are installed reboiler 4, reboiler 14 and reboiler 24, respectively. To each reboiler is added a heat so that the low-boiling components in the column bottom liquid are vaporized and the concentration of the low-boiling components in the column bottom liquid becomes a desired level or lower. The heat medium for the heat can be selected from known heat media used in a reboiler for these distillation columns, such as steam and heated hot oil, as appropriate.

From the demethanizer are obtained overhead gas 104 enriched with methane and lean in components heavier than methane and column bottom liquid 201 enriched with components heavier than methane and lean in methane. Bottom liquid 201 of the demethanizer is fed to deethanizer 11, distilled and separated into overhead gas 202 enriched with ethane and lean in components heavier than ethane and column bottom liquid 301 enriched with components heavier than ethane and lean in ethane.

At the top of the deethanizer 11, overhead gas 202 composed mainly of ethane is cooled by heat transfer medium 505 in condenser 12. That is, the cryogenic heat recovered from the liquefied natural gas is given to overhead gas 202. Thereby, deethanizer overhead gas 202 is condensed wholly, the condensate passes through reflux drum 13, and part of the condensate is fed back to the deethanizer as deethanizer reflux 204. The remainder of the condensate composed mainly of ethane is withdrawn as product ethane 205. From the bottom of the deethanizer, propane and heavier components (column bottom liquid 301) are separated, and they are fed to depropanizer 21.

In condenser 12, not the whole amount but only part of deethanizer overhead gas 202 may be condensed. For example, when the product ethane is withdrawn in gaseous state, only the portion of the overhead gas required for reflux 204 may be condensed.

At the top of depropanizer 21, overhead gas 302 composed mainly of propane is cooled by heat transfer medium 515 in condenser 22. That is, the cryogenic heat recovered from the liquefied natural gas is given to overhead gas 302. Thereby, depropanizer overhead gas 302 is condensed wholly, the condensate passes through reflux drum 23, and part of the condensate is fed back to the depropanizer as depropanizer reflux 304. The remainder of the condensate composed mainly of propane is withdrawn as product propane 305. From the bottom of the depropanizer, butane and heavier components (column bottom liquid 401) are withdrawn. Ordinarily, liquefied natural gas contains components heavier than butane only slightly. Therefore, depropanizer bottom liquid 401 is composed mainly of butane and is withdrawn as product butane.

The heat transfer media 506 and 516 heated in condensers 12 and 22, respectively, are returned to heat exchanger 5 for recovering cryogenic heat.

As described above, it is possible to circulate a heat transfer medium, recover a cryogenic heat by the heat transfer medium in the demethanizer and give, in the downstream deethanizer, etc., the cryogenic heat to their overhead gases by the heat transfer medium. Thus, efficient utilization of heat is made possible and further, by conducting indirect heat transfer via the heat transfer medium, the stability and reliability of operation can be enhanced.

As compared with, for example, a case wherein a feed liquefied natural gas at the inlet of a demethanizer is heated with a air-heated heater and the overhead gases of deethanizer, etc. are condensed with cooling water supplied from a cooling tower in the overhead gas condensers of the deethanizer, etc., no air-heated heater is required and the deethanization process, etc. can be conducted at a lower pressure according to the present invention, whereby energy saving and a lower cost can be achieved.

Owing to indirect heat transfer, even when the feed amount of feed liquefied natural gas fluctuates, it is possible to absorb the fluctuation by the circulation system of heat transfer medium, and to prevent the operation of deethanizer or depropanizer from being immediately affected and disturbed by the fluctuation. Also, even if there is breakage of the heat exchanger for recovering cryogenic heat, the feed liquefied natural gas or demethanizer-inside liquid does not flow into deethanizer and the deethanizer can be prevented from damage. Furthermore, in turndown operation, the super-cooling of heat transfer medium can be easily prevented by adjusting the flow rate of the heat transfer medium, and thus, the temperature of the reflux of deethanizer or the like can be easily kept at an appropriate level.

The recovery of cryogenic heat from demethanizer-inside liquid by the use of intermediate-stage heat exchanger 5 has further advantages as follows. For example, in a constitution where a heat exchanger for recovering cryogenic heat is installed in line 103, there is considered a case in which the fluid at the inlet of the heat exchanger for cryogenic heat recovery (the outlet of heat exchanger 2) becomes a gas-liquid two-phase flow when there has been a fluctuation in the feed amount of the feed liquefied natural gas or the amount of heat supplied by reboiler 4. On the other hand, when only the demethanizer-inside liquid is withdrawn from the demethanizer and fed to intermediate-stage heat exchanger 5, the fluid fed to the intermediate-stage heat exchanger is a liquid even if there has been any fluctuation. A heat exchange with which only a liquid is associated allows for safer operation as compared with a heat exchange with which gas-liquid two-phase flow is associated. Therefore, the heat exchange inside the intermediate-stage heat exchanger can be conducted excellently stably and the temperature of the heat transfer medium can be easily kept at an appropriate level. As a result, the disturbance of the operation of deethanizer can be excellently prevented. Also, since part (for example, about half) of the liquid flowing down in the demethanizer may be fed to the intermediate-stage heat exchanger, the amount of the liquid fed to the intermediate-stage heat exchanger can be secured even if there has been a certain fluctuation in the amount of the liquid flowing down in the demethanizer. Thus, the influence of such a fluctuation on the system of heat transfer medium can be excellently prevented.

Figure 2:
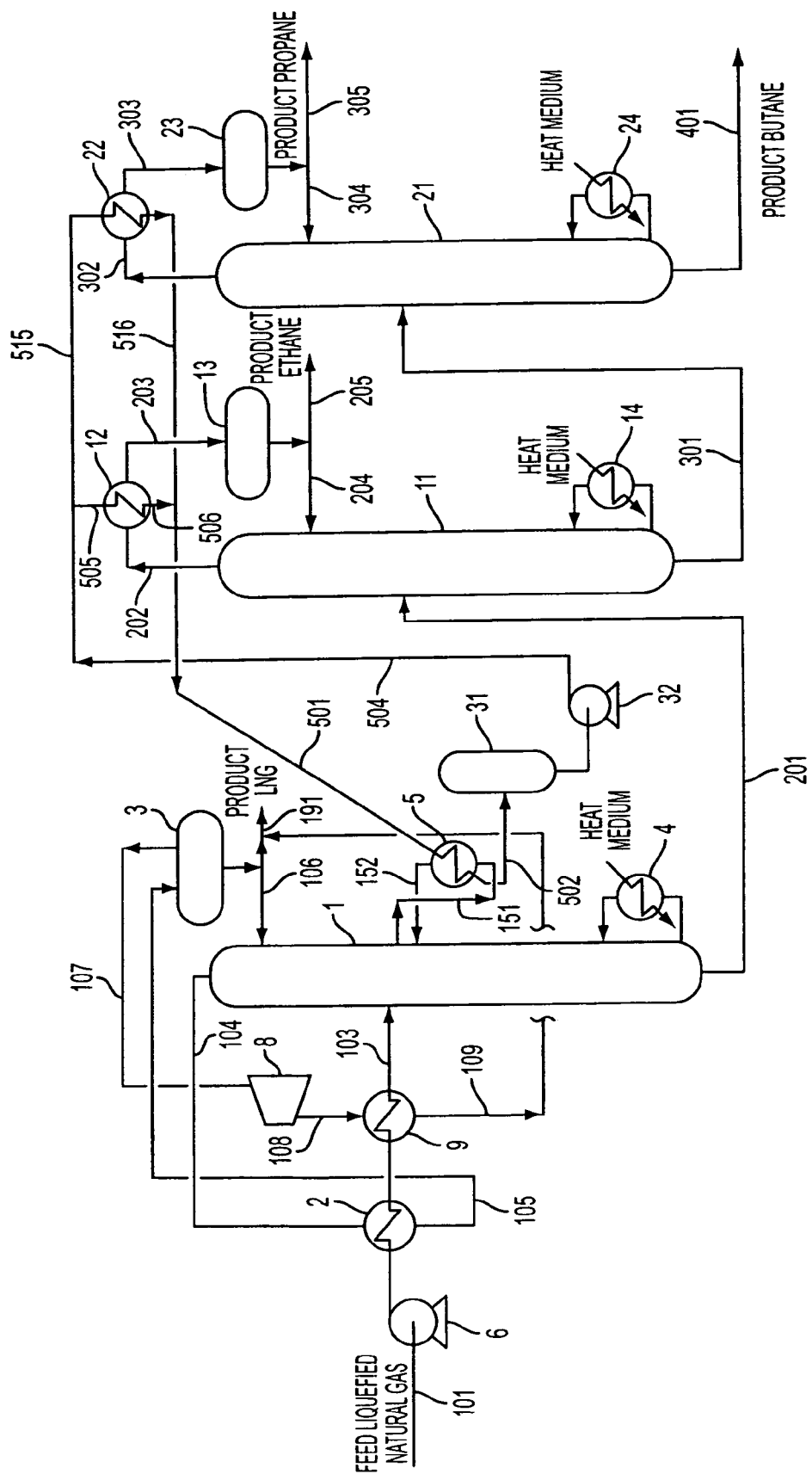
FIG. 2 is a flow diagram for explaining another embodiment of the apparatus of the present invention for separating hydrocarbons from a liquefied natural gas.

In FIG. 2 is shown other embodiment of the present invention. In this embodiment, demethanizer overhead gas 104 undergoes heat exchange with a feed liquefied natural gas in heat exchanger 2, whereby only part of the demethanizer overhead gas is liquefied. Fluid 105 after the heat exchange is sent to reflux drum 3 and separated into a gas and a liquid. At least part of the liquid separated is fed to the demethanizer as reflux 106. The remainder of the liquid is withdrawn as product liquefied natural gas 191. Gas (residue gas) 107 separated in reflux drum 3 is pressurized by residue gas compressor 8. Pressurized gas 108 undergoes heat exchange with the feed liquefied natural gas in heat exchanger 9 for pressurized residue gas, and thereby is cooled and liquefied wholly. Pressurized and liquefied residue gas 109 leaving heat exchanger 9 for pressurized residue gas is withdrawn as product liquefied natural gas 191 together with the part of the liquid separated in the reflux drum.

In this embodiment, by using part of the demethanizer overhead gas having a higher methane concentration owing to distillation as a reflux, it is possible to increase the methane concentration in the overhead gas and improve the separation efficiency in the demethanizer. Also, owing to the presence of the reflux, the fluctuation in the total amount of the liquid flowing down in the demethanizer is relatively small even if there has been a fluctuation in the amount of the feed liquefied natural gas fed. Therefore, there is an advantage that the fluctuation in the feed amount of the feed liquefied natural gas gives far less influence on the operations of the deethanizer, etc.

The constitution of the embodiment shown in FIG. 2 other than described above can be made the same as the embodiment of FIG. 1.

The embodiments each conducting demethanization, deethanization and depropanization have been explained above. However, depropanization need not be conducted and only demethanization and deethanization may be conducted.

EXAMPLES

The present invention is described in more detail below by way of Examples. However, the present invention is in no way restricted thereby. Incidentally, (A) in pressure unit means an absolute pressure.

Example 1

In this Example is explained a process having a flow shown in FIG. 2, for recovering ethane, propane and butane from feed liquefied natural gas. Here, feed liquefied natural gas 101 having a pressure of 0.5 MPa (A) and a temperature of −152° C. is introduced into the present process at a flow rate of 625 tons/hour. The feed liquefied natural gas had a composition shown in Table 1.

TABLE 1

| Composition of feed liquefied natural gas (mol %) | |
|---|---|
| $N_2$ | 0.46 |
| Methane | 89.79 |
| Ethane | 6.47 |
| Propane | 2.23 |
| Butane | 1.05 |
| Components heavier than butane | 0.00 |
| Total | 100.00 |

The feed liquefied natural gas is pressurized by feed liquefied natural gas pump 6 and undergoes heat exchange with the overhead gas of demethanizer at overhead gas condenser 2 and pressurized residue gas heat exchanger 9. Thereby, demethanizer feed 103 is heated up to about −100° C. and fed to the 12th tray of demethanizer 1.

The demethanizer has trays of 23 stages in terms of theoretical stage number inside and is operated at the top under the conditions of a pressure of from 1.5 MPa (A) to 3.5 MPa (A) and a temperature of from −110° C. to −90° C.

At the 16th tray of the demethanizer is installed only one intermediate-stage heat exchanger 5. Part of the liquid of about −100° C. flowing down in the demethanizer is withdrawn (line 151) and undergoes, in the heat exchanger, heat exchange with methanol 501 used as a heat transfer medium. The methanol is cooled down to −45° C. at the outlet (line 502) of the intermediate-stage heat exchanger of the demethanizer, passes through surge drum 31 and circulation pump 32, and is used as a cooling medium for the overhead gas condensers of deethanizer 11 and depropanizer 21. The deethanizer is operated at the top at a pressure of 1.65 MPa (A) and at a temperature of −14.6° C., and the depropanizer is operated at a pressure of 0.74 MPa (A) and at a temperature of 16.4° C.

In Table 2 is shown a comparison of performances when the operating pressure of the demethanizer was varied in three cases as Examples 1-1, 1-2 and 1-3. When the operating pressure of the demethanizer is increased to a higher level, the power of the compressor can be reduced but the recovery rate of ethane (the proportion of the amount of product ethane 205 to the amount of ethane contained in feed liquefied natural gas 101) decreases. On the other hand, in operation at a lower pressure, the weight of the distillation column can be reduced and the manufacturing cost of distillation column can be reduced. Any case of these can be carried out and the operating pressure of the demethanizer can be determined in overall consideration of initial investment cost, running cost, etc.

TABLE 2

Comparison of performances associated with demethanizer

| | | Example No. | | |
|---|---|---|---|---|
| | | 1-1 | 1-2 | 1-3 |
| Operating pressure of demethanizer (top) | MPa (A) | 1.5 | 2.2 | 3.0 |
| Recovery rate of ethane | % | 98.5 | 98.2 | 96.1 |
| Diameter of column | mm | 5,300 | 5,500 | 7,200 |
| Manufacturing cost of column | — | Low | Low | High |
| Duty of intermediate-stage heat exchanger 5 | MW | 19.1 | 19.4 | 19.9 |
| Duty of reboiler 4 | MW | 13.8 | 21.0 | 30.2 |
| Power of compressor 8 | MW | 3.5 | 2.2 | 1.0 |

Example 2

Figure 3:
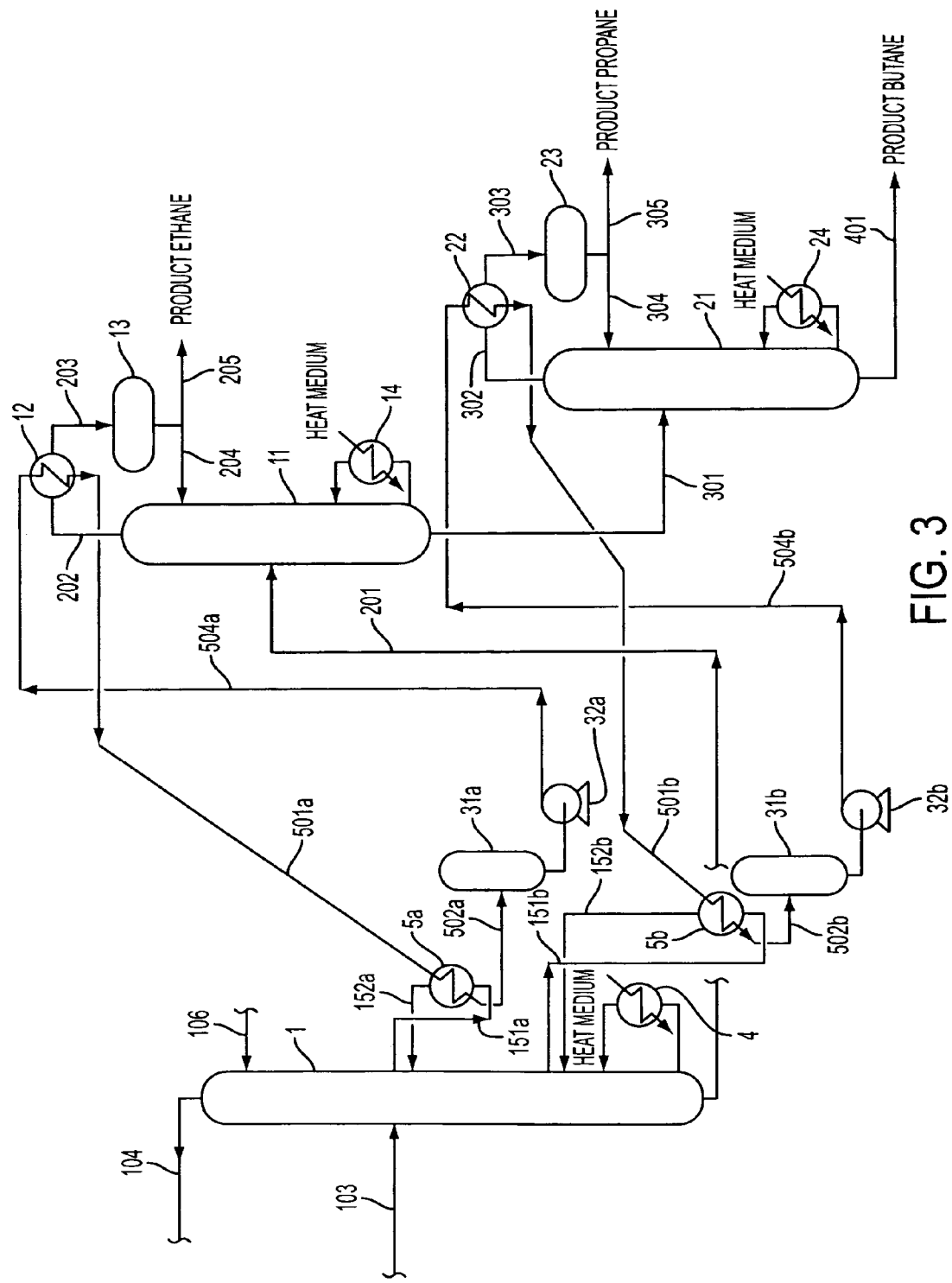
FIG. 3 is a flow diagram for explaining further embodiment of the apparatus of the present invention for separating hydrocarbons from a liquefied natural gas.

In this Example, as shown in FIG. 3, two intermediate-stage heat exchangers for demethanizer are installed in order to give the heat transfer medium temperature levels more appropriate for cooling medium used in the overhead gas condensers of deethanizer and depropanizer. That is, there are independently installed a heat transfer medium circulation system for cooling the deethanizer overhead gas and a heat transfer medium circulation system for cooling the depropanizer overhead gas and, in each of these heat transfer medium circulation systems, an intermediate-stage heat exchanger is installed. For example, when the deethanizer is operated at a lower pressure for the lighter weight and smaller size of the deethanizer, it is necessary to use a cooling medium of lower temperature at the overhead gas condenser of the deethanizer. On the other hand, even if the depropanizer has been designed for an even lower pressure, it is not required to use a cooling medium as cold as required in the deethanizer. Since the temperature levels required for condensing the overhead gases of deethanizer and depropanizer are different from each other, by installing two intermediate-stage heat exchangers at the demethanizer as mentioned above, it is possible to feed cooling media having more appropriate temperature levels to the deethanizer and the depropanizer.

In FIG. 3 are shown a demethanizer, lines downstream of demethanizer bottom liquid 201, and circulation lines of heat transfer media. The line upstream of demethanizer feed 103, the line downstream of demethanizer overhead gas 104, and the line upstream of demethanizer reflux 106 are the same as in the embodiment of Example 1 shown in FIG. 2 and are not shown in FIG. 3.

Here, feed liquefied natural gas 103 having the same composition as in Example 1 is introduced into the 12th tray of the demethanizer under the same temperature and pressure conditions as in Example 1.

The operating pressures of the top portions of the deethanizer and the depropanizer are, respectively, 0.40 MPa (A) and 0.35 MPa (A) in Example 2-1 and, in Example 2-2, 1.65 MPa (A) and 0.40 MPa (A). In Tables 3 and 4 are shown comparisons between these cases and Example 1-2.

Figure 4:
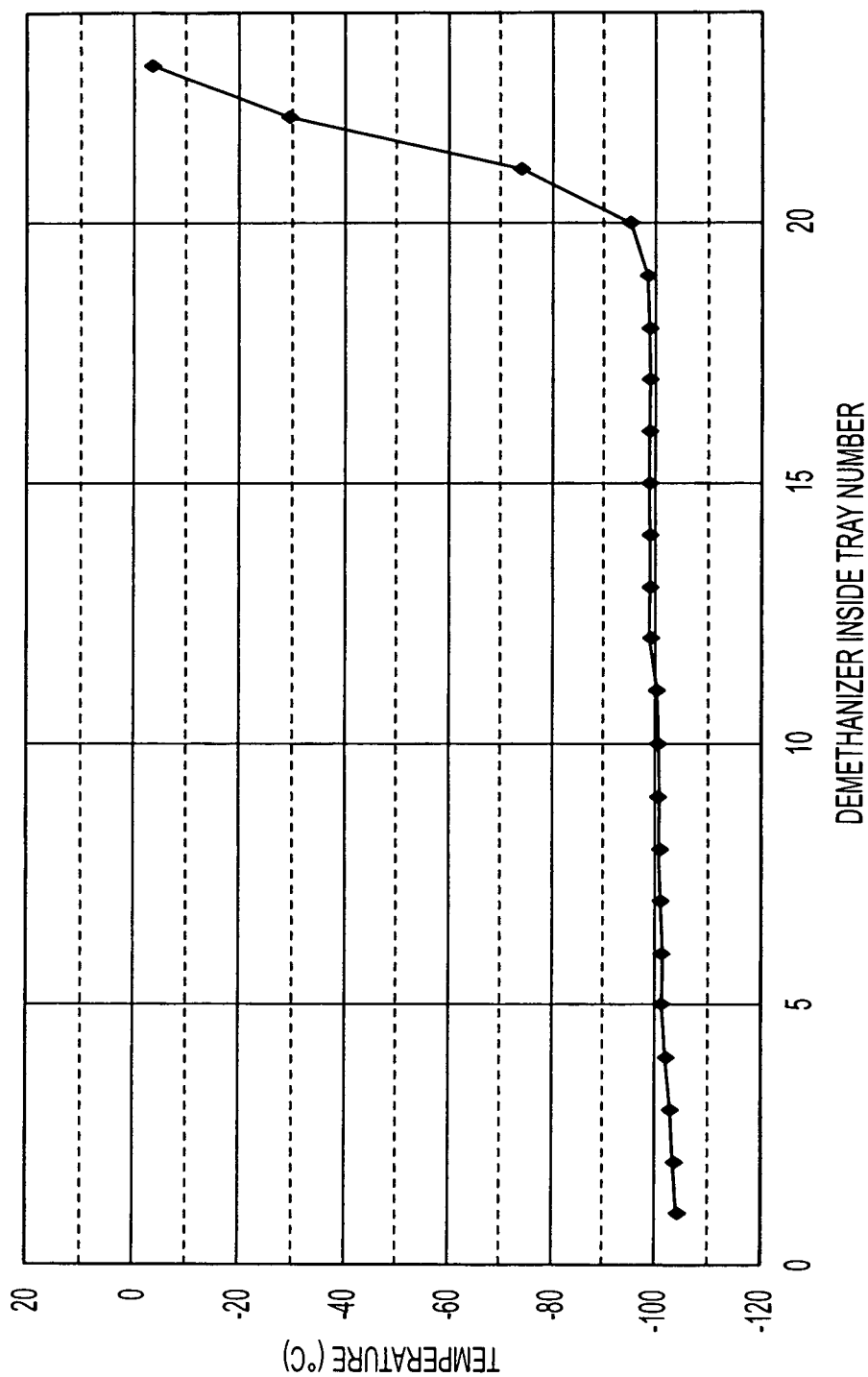
FIG. 4 is a graph showing an example of the temperature distribution of demethanizer inside.

There is shown, in FIG. 4, a demethanizer-inside temperature distribution when no intermediate-stage heat exchanger is installed at the demethanizer. As shown in this figure, the demethanizer-inside temperature is as low as –100° C. at the trays of 1st to 20th but rises sharply at the trays lower than that. When the operating pressure of deethanizer 11 is lowered from 1.65 MPa (A) to 0.4 MPa (A) as shown in Table 3, the operating temperature at the deethanizer top becomes –58° C.; therefore, intermediate-stage heat exchanger 5a for deethanizer overhead gas condenser can be installed between the 12th tray (which is a feed tray) and the 20th tray (which can recover a cryogenic heat of –100° C.).

Meanwhile, in depropanizer 21, the effect of cost reduction is relatively small even if the operating pressure has been reduced, as shown in Table 4. Therefore, depropanizer 21 may be designed at a pressure of 0.74 MPa (A). Since the cryogenic heat required in this case is 16.4° C., intermediate-stage heat exchanger 5b can be installed lower than the 20th tray.

When two intermediate-stage heat exchangers are installed, the number of apparatuses of heat transfer medium circulation systems is inevitably two times the number in Example 1. Further, since deethanizer 11 handles a liquid of lower temperature than in Example 1, the material for deethanizer 11 need be selected from those capable of withstanding low temperatures, such as stainless steel. Meanwhile, effects of reduction in transportation cost and construction cost and the like can be expected owing to lighter weight and smaller size.

The number of intermediate-stage heat exchangers as well may be determined in overall consideration of economical efficiency.

TABLE 3

Comparison of performances of deethanizer

| | | Example No. | |
|---|---|---|---|
| | | 2-1 | 1-2 |
| Operating pressure of deethanizer (top) | MPa (A) | 0.40 | 1.65 |
| Operating temperature (deethanizer top) | ° C. | –58.0 | –14.6 |
| Column diameter | mm | 2,700 | 3,400 |
| Material | — | 3.½ Ni steel or stainless steel | Killed steel |

TABLE 4

Comparison of performances of depropanizer

| | | Example No. | |
|---|---|---|---|
| | | 2-2 | 1-2 |
| Operating pressure of depropanizer (top) | MPa (A) | 0.40 | 0.74 |
| Operating temperature (depropanizer top) | ° C. | –4.4 | 16.4 |
| Column diameter | mm | 2,400 | 2,300 |
| Material | — | Carbon steel | Carbon steel |

Comparative Example 1

Figure 5:
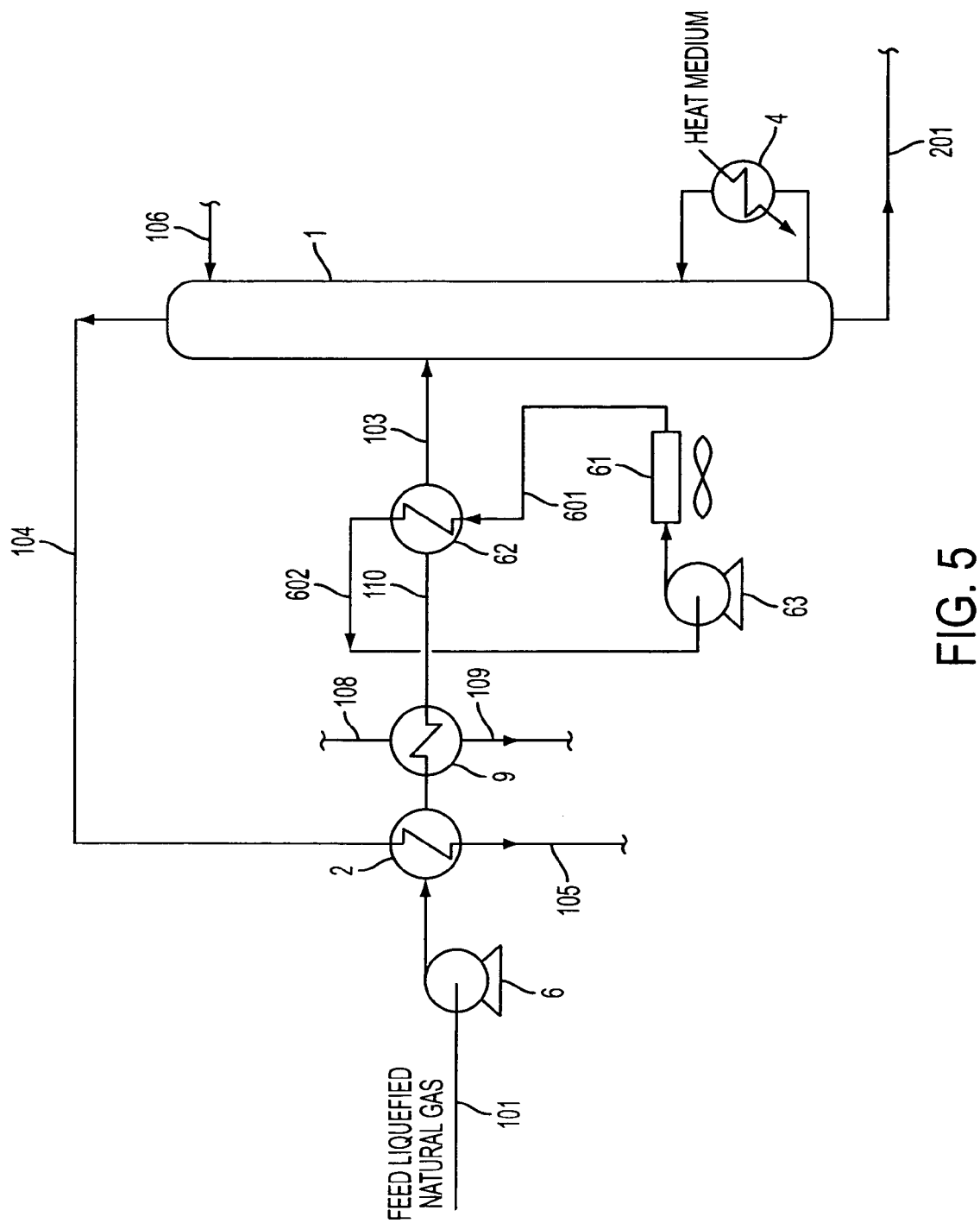
FIG. 5 is a flow diagram for explaining the apparatus for separation of hydrocarbons, employed in Comparative Example 1.

There was investigated a process of heating a demethanizer feed by a sensible heat of air, as shown in FIG. 5, in place of conducting the recovery of cryogenic heat and the condensation of deethanizer overhead gas and depropanizer overhead gas by using a heat transfer medium. Demethanizer feed preheater 62 is installed in demethanizer feed line 103, and there was fed, to the preheater, antifreezing solution (glycol solution) 601 heated by air-heated heater 61, to heat the demethanizer feed. Antifreezing solution 602 having heated the demethanizer feed is pressurized by antifreezing solution circulation pump 63 and fed to air-heated heater 61.

As a cooling medium for cooling the overhead gas at each of the deethanizer overhead gas condenser and the depropanizer overhead gas condenser, there was used a product liquefied natural gas in place of a heat transfer medium.

Other than mentioned above, the process of Comparative Example 1 is the same as that of Example 1 shown in FIG. 2.

In FIG. 5, there are omitted the downstream of line 105, the upstream of line 106, the upstream of line 108 and the downstream of line 109. The downstream of deethanizer feed 201 is also omitted and there are also omitted the cooling systems by the above-mentioned cooling medium for the deethanizer overhead gas condenser and the depropanizer overhead gas condenser.

The conditions of the liquefied natural gas fed to demethanizer 1 were the same as in Example 1. In Table 5 are shown the conditions of the apparatuses used, compared with those used in Example 1-2. In the process shown in FIG. 2, there are intermediate-stage heat exchanger 5 of demethanizer, heat transfer medium surge drum 31 and heat transfer medium circulation pump 32. On the other hand, in case that an air-heated heater is installed, there are needed air-heated heater 61, demethanizer feed preheater 62 and antifreezing solution circulation pump 63. There are also needed cooling systems for condensing the overhead gases of deethanizer and depropanizer; however, they were not considered here.

When the air-heated heater is installed, as compared with when the intermediate-stage heat exchanger is installed, the equipment cost is 1.4 times that of the latter case. Further, the installation area for the air-heated heater is very large, supports for supporting the heater and the sufficient space for installing it are needed, and the investment cost therefor is needed. Furthermore, when the powers of the two cases are compared for comparison of operating costs, an electric power of 320 kW is needed additionally when the air-heated heater is used. It is clear from these that the installment of an intermediate-stage heat exchanger is lower in each of investment cost and operating cost.

TABLE 5

Comparison of apparatuses

| Example No. | | Example 1-2 Installment of intermediate-stage heat exchanger | Comparative Example 1 Installment of air-heated heater |
|---|---|---|---|
| Intermediate-stage heat exchanger 5, or feed preheater 62 | Amount of heat exchange | 20 MW | 20 MW |
|  | Heat transfer area | 860 m² | 700 m² |
|  | Material | Stainless steel | Stainless steel |
| Heat transfer medium circulation pump 32, or Antifreezing solution circulation pump 63 | Flow rate | 1000 m³/h | 2000 m³/h |
|  | Liquid head | 35 m | 35 m |
|  | Specific gravity | 0.85 | 1.0 |
|  | Power | 160 kW | 300 kW |
| Air-heated heater 61 | Amount of heat exchange | — | 20 MW |
|  | Heat transfer area | — | 1350 m² |
|  | Fan power | — | 180 kW |
| Surge drum 31 | Size | 2 m (diameter) × 6 m (height) | — |
| Total equipment cost | | 1 (base) | 1.4 |

Comparative Example 2

There was investigated a case in which, in place of conducting the recovery of cryogenic heat and the condensation of deethanizer overhead gas and depropanizer overhead gas by using a heat transfer medium, two intermediate-stage heat exchangers were installed and the deethanizer overhead gas and the depropanizer overhead gas were directly introduced into the intermediate-stage heat exchangers, respectively, for heat exchange with demethanizer-inside liquid.

Figure 6:
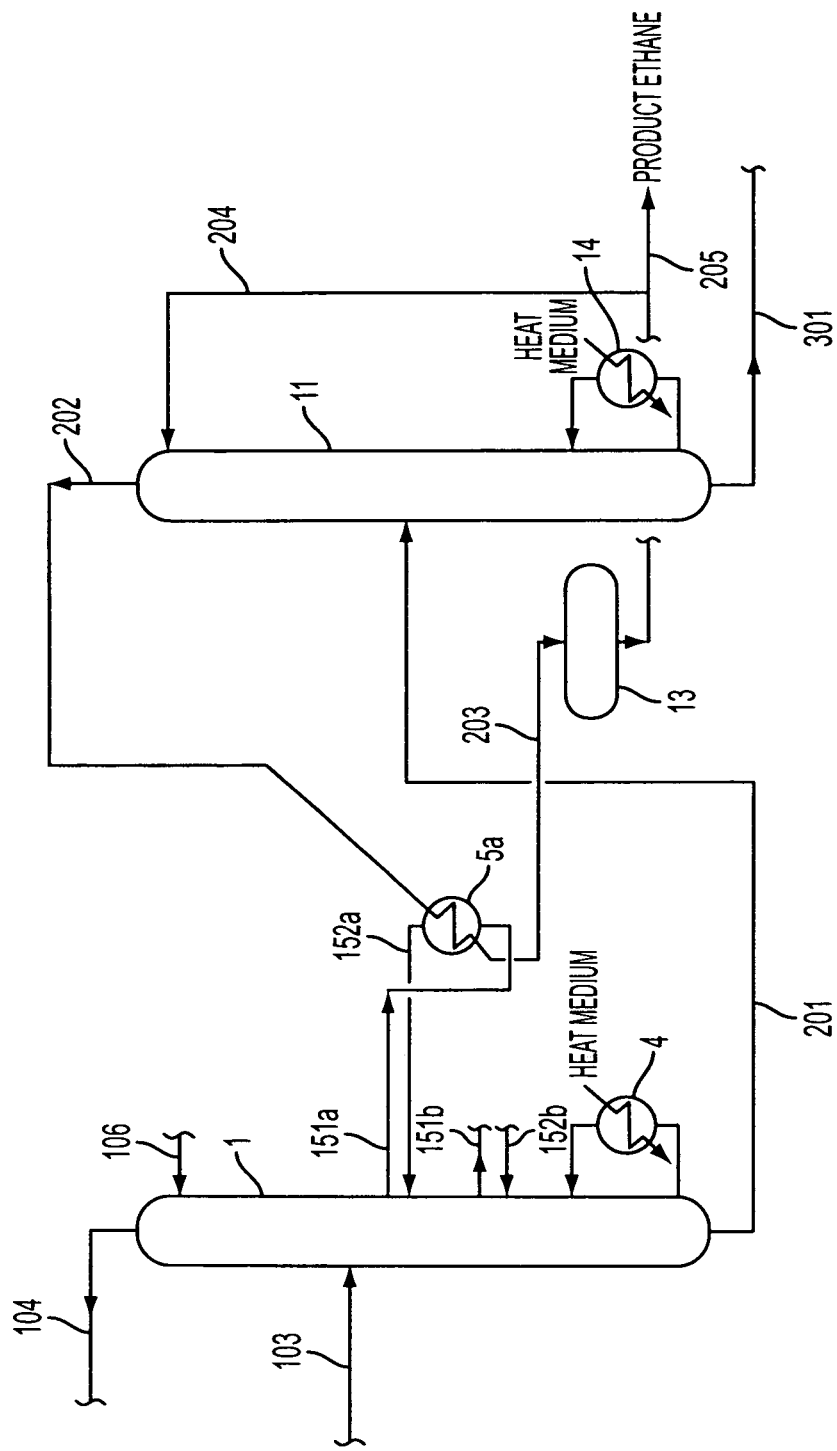
FIG. 6 is a flow diagram for explaining the apparatus for separation of hydrocarbons, employed in Comparative Example 2.

As shown in FIG. 6, deethanizer overhead gas 202 is introduced into intermediate-stage heat exchanger 5a, is cooled therein by demethanizer-inside liquid 151a, and passes through deethanizer reflux drum 13; part of the fluid leaving the reflux drum is returned to the deethanizer as deethanizer reflux 204; and the remainder becomes product ethane 205.

In FIG. 6 are not shown a depropanizer and a heat transfer medium circulation system (including an intermediate-stage heat exchanger) for cooling a depropanizer overhead gas. However, similarly to the above-mentioned case of the deethanizer, the depropanizer overhead gas is introduced into the intermediate-stage heat exchanger (not shown), is cooled therein by heat exchange with demethanizer-inside liquid 151b, and passes through a depropanizer reflux drum (not shown); part of the fluid leaving the reflux drum is returned to the depropanizer as depropanizer reflux; and the remainder becomes a product propane.

Other than mentioned above, the process of Comparative Example 2 shown in FIG. 6 is the same as that of Example 2 shown in FIG. 3. In FIG. 6 are omitted the upstream of line 103, the downstream of line 104, the upstream of line 106, the downstream of line 151b, the upstream of line 152b and the downstream of line 301.

In Table 6 is shown a comparison between direct heat exchange and indirect heat exchange in intermediate-stage heat exchangers. In the intermediate-stage heat exchanger of direct heat exchange, the heat transfer area of the overhead gas condenser may become excessive in turndown operation (partial-load operation) and the overhead gas of deethanizer or depropanizer may be cooled excessively (this does not occur in normal operation). The deethanizer and the depropanizer may be made of carbon steel or killed steel; however, when an excessively cooled reflux is fed to such a distillation column, the column may undergo a thermal shock of a temperature lower than the allowable lower limit temperature of such a material and there arises a fear in safety.

Further, when the intermediate-stage heat exchanger breaks, a liquefied natural gas having a temperature of as low as −100° C. flows into the deethanizer or the depropanizer and may give a thermal shock. As a countermeasure therefor, it is considered to manufacture the deethanizer or the depropanizer using a material capable of withstanding a low temperature of −100° C., such as stainless steel, however, this results in an increase in manufacturing cost and a reduction in economical efficiency.

On the other hand, in the intermediate-stage heat exchangers using a heat transfer medium such as methanol, because the cooling temperature of the heat transfer medium can be controlled, it is possible to maintain a stable temperature of a cryogenic heat in feeding a cryogenic heat to the overhead gas condenser of a deethanizer or a depropanizer.

Also, because the flow rate of the heat transfer medium flowing into the overhead gas condenser of each distillation column can be visualized by flow control, the deethanizer and the depropanizer can be controlled easily.

Furthermore, by making the operating pressure and design pressure of the heat transfer medium lower than the operating pressures of the demethanizer, the deethanizer and the depropanizer, it is possible to prevent the heat transfer medium from flowing into the distillation columns even if there are breakage of heat exchanger and resultant leakage of heat transfer medium, and to discharge the heat transfer medium quickly out of the system from, for example, a relief valve fitted to a heat transfer medium surge drum.

TABLE 6

Comparison between direct heat exchange and indirect heat exchange in intermediate-stage heat exchangers

| Example No. | Comparative Example 2 Direct heat exchange | Example 2-1 Indirect heat exchange |
|---|---|---|
| Stability in cryogenic heat feeding | Inferior | Superior |
| Control of distillation column | Inferior | Superior |
| Thermal shock problem | Present | Not present |

The present invention can be suitably used for separation and recovery of hydrocarbons such as ethane from a liquefied natural gas.

The invention claimed is:

1. A process for separating hydrocarbons from a liquefied natural gas, comprising:
 (a) a step of distilling a feed liquefied natural gas in a first distillation column to separate the feed liquefied natural gas into a fraction enriched with methane and a fraction enriched with components heavier than methane, said first distillation column having a bottom reboiler;
 (b) a step of distilling the fraction enriched with components heavier than methane in a second distillation column to separate the fraction enriched with components heavier than methane into an overhead gas enriched with ethane and a fraction enriched with components heavier than ethane;
 (c) a step of recovering cryogenic heat of the liquid inside the first distillation column in a first heat exchanger that is provided separately from the bottom reboiler of the first distillation column, wherein the heat exchanger is in communication with a circulating heat transfer medium that circulates in a closed loop, the heat transfer medium is in a liquid state in the closed loop independent of the feed liquefied natural gas and the liquid inside the first distillation column;
 (d) a step of condensing at least a part of the overhead gas of the second distillation column in a first condenser by using at least a part of the recovered cryogenic heat in the circulating heat transfer medium from step (c); and
 (g) a step of returning the circulating heat transfer medium through the closed loop from step (d) to step (c).

2. A process according to claim 1, wherein step (c) comprises withdrawing liquid from inside the first distillation column at a position of the first distillation column lower than the position where the feed liquefied natural gas is fed into the first column, recovering the cryogenic heat of the withdrawn liquid using the circulating heat transfer medium, and returning the withdrawn liquid into the first distillation column.

3. A process according to claim 1, further comprising:
 (e) a step of distilling the fraction enriched with components heavier than ethane in a third distillation column to separate the fraction enriched with components heavier than ethane into an overhead gas enriched with propane and a fraction enriched with components heavier than propane;
 (f) a step of condensing at least a part of the overhead gas of the third distillation column in a second condenser by using another part of the recovered cryogenic heat in the circulating heat transfer medium from step (c); and
 (h) a step of returning the circulating heat transfer medium through the closed loop from step (f) to step (c).

4. An apparatus for separating hydrocarbons from a liquefied natural gas, comprising:
 a first distillation column for distilling a feed liquefied natural gas to separate the feed liquefied natural gas into a fraction enriched with methane and a fraction enriched with components heavier than methane, said first distillation column having a bottom reboiler;
 a second distillation column for distilling the fraction enriched with components heavier than methane to separate the fraction enriched with components heavier than methane into an overhead gas enriched with ethane and a fraction enriched with components heavier than ethane;
 a first heat exchanger for recovering the cryogenic heat of the liquid inside the first distillation column by using a circulating heat transfer medium that circulates in a first closed loop in communication with the first heat exchanger, wherein the heat transfer medium is in a liquid state within the first closed loop independent of the feed liquefied natural gas and the liquid inside the first distillation column, and the first heat exchanger is provided separately from the bottom reboiler of the first distillation column; and
 a first condenser in communication with the first closed loop, the first condenser for condensing at least a part of the overhead gas of the second distillation column by using at least a part of the recovered cryogenic heat in the circulating heat transfer medium.

5. The apparatus according to claim 4, wherein the first distillation column is provided with a line for withdrawing liquid from inside the first distillation column at a position of the first distillation column lower than the position where the feed liquefied natural gas is fed and returning the withdrawn liquid into the first distillation column, and said first heat exchanger is provided in said line.

6. An apparatus according to claim 4, further comprising:
 a third distillation column for distilling the fraction enriched with components heavier than ethane to separate the fraction enriched with components heavier than ethane into a fraction enriched with propane and a fraction enriched with components heavier than propane; and
 a second condenser in communication with the first closed loop, the second condenser for condensing at least a part of the overhead gas of the third distillation column by using another part of the recovered cryogenic heat in the circulating heat transfer medium.

7. A process according to claim 2, further comprising:
 (e) a step of distilling the fraction enriched with components heavier than ethane in a third distillation column to separate the fraction enriched with components heavier than ethane into an overhead gas enriched with propane and a fraction enriched with components heavier than propane;
 (f) a step of condensing at least a part of the overhead gas of the third distillation column in a second condenser by using another part of the recovered cryogenic heat in the circulating heat transfer medium from step (c); and (h) a step of returning the circulating heat transfer medium through the closed loop from step (f) to step (c).

8. An apparatus according to claim 5, further comprising:
a third distillation column for distilling the fraction enriched with components heavier than ethane to separate the fraction enriched with components heavier than ethane into a fraction enriched with propane and a fraction enriched with components heavier than propane; and
a second condenser in communication with the first closed loop, the second condenser for condensing at least a part of the overhead gas of the third distillation column by using at least a part of recovered cryogenic heat in the circulating heat transfer medium.

9. The process according to claim 1, wherein the circulating heat transfer medium in step (c) has a freezing point of −90° C. or less and a boiling point of 50° C. or more.

10. The process according to claim 1, wherein the circulating heat transfer medium in step (c) comprises methanol in the liquid state.

11. The apparatus according to claim 4, wherein the circulating heat transfer medium that circulates in a first closed loop has a freezing point of −90° C. or less and a boiling point of 50° C. or more.

12. The apparatus according to claim 4, the circulating heat transfer medium that circulates in a first closed loop comprises methanol in the liquid state.

\* \* \* \* \*